United States Patent
Damaser et al.

(10) Patent No.: US 11,957,468 B2
(45) Date of Patent: Apr. 16, 2024

(54) STANDARDIZED MEASUREMENT OF PHYSIOLOGICAL PRESSURES USING AN AIR-CHARGED CATHETER APPARATUS

(71) Applicants: THE CLEVELAND CLINIC FOUNDATION, Cleveland, OH (US); The United States Government as represented by the Department of Veterans Affairs, Washington, DC (US)

(72) Inventors: Margot S. Damaser, Cleveland Hts., OH (US); Hassan K. Awada, Pittsburgh, PA (US); Paul C. Fletter, Mt. Prospect, IL (US); Mitchell Cooper, Jersey City, NJ (US); Paul J. Zaszczurynski, Sycamore, IL (US)

(73) Assignees: THE CLEVELAND CLINIC FOUNDATION, Cleveland, OH (US); The United States Government as represented by the Department of Veterans Affairs, Washington, DC (US)

( * ) Notice: Subject to any disclaimer, the term of this patent is extended or adjusted under 35 U.S.C. 154(b) by 578 days.

(21) Appl. No.: 16/742,147

(22) Filed: Jan. 14, 2020

(65) Prior Publication Data
US 2020/0146608 A1   May 14, 2020

Related U.S. Application Data

(62) Division of application No. 13/623,981, filed on Sep. 21, 2012, now Pat. No. 10,537,274.
(Continued)

(51) Int. Cl.
*A61B 5/03*   (2006.01)
*A61B 5/00*   (2006.01)
(Continued)

(52) U.S. Cl.
CPC .............. *A61B 5/205* (2013.01); *A61B 5/036* (2013.01); *A61B 5/0823* (2013.01); *A61B 5/7278* (2013.01); *A61B 5/742* (2013.01)

(58) Field of Classification Search
CPC ............. A61M 2025/0001; A61M 2025/0002; A61M 25/00; A61B 5/02156;
(Continued)

(56) References Cited

U.S. PATENT DOCUMENTS 5,694,946 A   12/1997 Tenerz et al.
5,951,497 A   9/1999 Wallace et al.
(Continued)

OTHER PUBLICATIONS

Walter, James S., et al. "A balloon-tipped catheter for measuring urethral pressures." The journal of spinal cord medicine 32.5 (2009): 578-582.
(Continued)

*Primary Examiner* — Devin B Henson
*Assistant Examiner* — H. Q. Nguyen
(74) *Attorney, Agent, or Firm* — Tarolli, Sundheim, Covell & Tummino LLP

(57) ABSTRACT

Systems and methods are provided for providing a standardized pressure value representing a transient pressure event within a region of interest within a living body. An air-charged catheter is configured to record pressure data representing the region of interest. A measurement assembly includes a parameter calculation component configured to calculate at least a peak pressure representing the transient pressure event and a time to peak pressure, representing the time necessary to reach the peak pressure, from the recorded pressure data. A standardization component is configured to calculate the standardized pressure value as a function of the peak pressure and the time to peak pressure. A user interface
(Continued)

is configured to display at least the standardized pressure value at an associated display.

10 Claims, 3 Drawing Sheets

Related U.S. Application Data

(60) Provisional application No. 61/537,855, filed on Sep. 22, 2011.

(51) Int. Cl.
*A61B 5/08* (2006.01)
*A61B 5/20* (2006.01)

(58) Field of Classification Search
CPC ..... A61B 5/6852; A61B 5/205; A61B 5/0084; A61B 5/0823; A61B 2560/066
See application file for complete search history.

(56) References Cited

U.S. PATENT DOCUMENTS

| 6,231,524 | B1 | 5/2001 | Wallace et al. |
| 7,252,631 | B2 | 8/2007 | Tracey |
| 7,255,673 | B2 | 8/2007 | Ulmsten et al. |
| 2003/0060711 | A1 | 3/2003 | Michaeli |
| 2004/0024294 | A1 | 2/2004 | Wellnhofer |
| 2006/0047201 | A1 | 3/2006 | Eide |
| 2010/0137736 | A1 | 6/2010 | Addington et al. |
| 2011/0257593 | A1 | 10/2011 | Kalpin et al. |

OTHER PUBLICATIONS

Zehnder, et al. Air-Charged and microtransducer urodynamic . . . International Urogynecology Journal of Urology, vol. 180, 1013-1017, Sep. 2008.

Pollak, Jennifer T., et al. "Air-charged and microtransducer urodynamic catheters in the evaluation of urethral function." International Urogynecology Journal 15.2 (2004): 124-128.

STANDARDIZED MEASUREMENT OF PHYSIOLOGICAL PRESSURES USING AN AIR-CHARGED CATHETER APPARATUS

RELATED APPLICATION

This application is a divisional of U.S. patent application Ser. No. 13/623,981, filed 21 Sep. 2012, which claims priority from U.S. Provisional Application No. 61/537,855, filed 22 Sep. 2011, the subject matter of each of which is incorporated herein by reference in its entirety.

TECHNICAL FIELD

The present invention relates generally to the field of medical sensing, and more particularly to systems and methods for measuring physiological pressures with an air-charged pressure sensing catheter apparatus.

BACKGROUND OF THE INVENTION

Air-charged pressure sensing catheters provide a number of advantages over more traditional water-filled or microtip pressure transducer technologies. For example, air-charged catheters are relatively inexpensive, easy to use, disposable, and significantly less subject to artifact. Due to these advantages, use of these catheters for pressure sensing applications has become increasingly prominent. For example, around seventy percent of the pressure transducers currently utilized in the United States urological market are air-charged catheters.

SUMMARY OF THE INVENTION

In accordance with one aspect of the present invention, a system is provided for generating a standardized pressure value representing a transient pressure event within a region of interest within a living body. An air-charged catheter is configured to record pressure data representing the region of interest. A measurement assembly includes a parameter calculation component configured to calculate at least a peak pressure representing the transient pressure event and a time to peak pressure, representing the time necessary to reach the peak pressure, from the recorded pressure data. A standardization component is configured to calculate the standardized pressure value as a function of the peak pressure and the time to peak pressure. A user interface is configured to display at least the standardized pressure value at an associated display.

In accordance with another aspect of the present invention, a method is provided for recording a standardized pressure representing a transient pressure event inside a region of interest with an air-charged pressure sensing catheter. The air-charged catheter is inserted into a region of interest. Pressure data is collected over a time period including the transient pressure event. A peak pressure is determined as the difference between a maximum pressure and a baseline pressure. The standardized pressure, representing a peak pressure that would be expected for a water-filled catheter given the determined peak pressure, is calculated as a function of the determined peak pressure. At least the standardized pressure is displayed to an operator at an associated display.

In accordance with still another aspect of the present invention, a non-transitory computer readable medium stores machine executable instructions for providing a standardized pressure value from pressure data representing a transient pressure event within a region of interest within a living body taken with an air-charger catheter. The instructions include a parameter calculation component configured to calculate at least a peak pressure, $P_{peak}$, representing a maximum recorded pressure, in centimeters of water, during the transient pressure event and a time to peak pressure, $T_{PP}$, representing the time necessary to reach the peak pressure at the air-charged catheter, from the recorded pressure data. A standardization component is configured to calculate a standardized pressure value, $P_{Std}$, representing a peak pressure that would be expected for a water-filled catheter given the calculated peak pressure, such that:

$$P_{Std} = \frac{P_{peak} * T_{PP}^{1.184}}{T_{PP}^{1.184} - 0.03}.$$

BRIEF DESCRIPTION OF THE DRAWINGS

The foregoing and other features of the present invention will become apparent to those skilled in the art to which the present invention relates upon reading the following description with reference to the accompanying drawings, in which.

DETAILED DESCRIPTION

Figure 1:
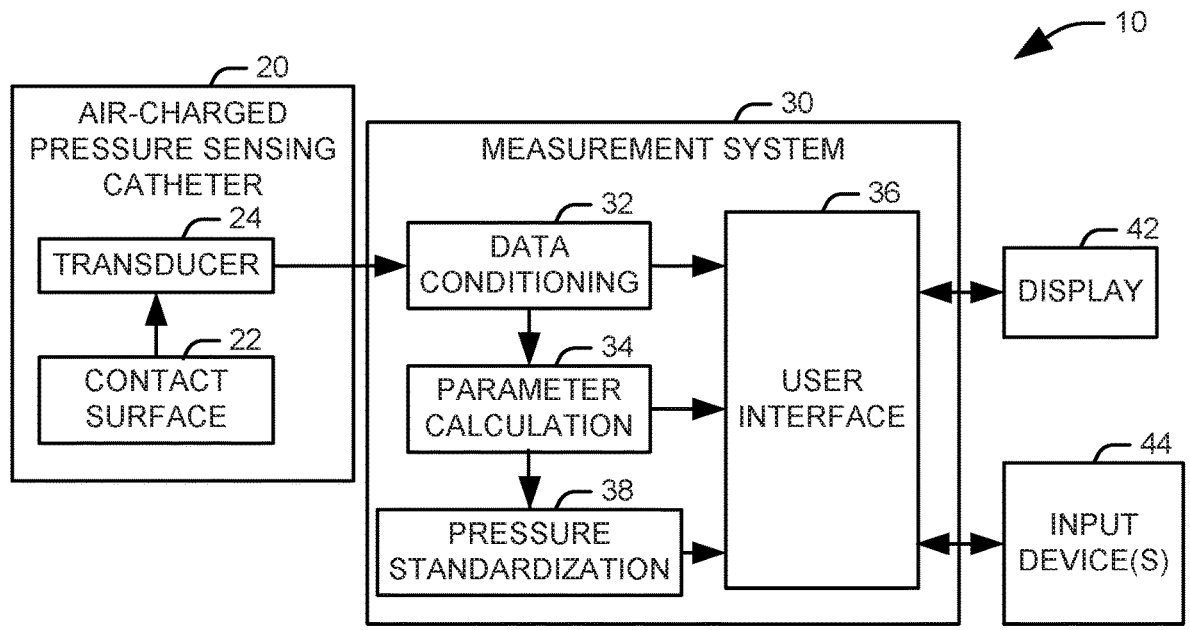
FIG. 1 illustrates a system for determining a pressure within a region of interest of a human body associated with a transient pressure event in accordance with an aspect of the present invention.

FIG. 1 illustrates a system 10 for determining a pressure within a region of interest of a human body associated with a transient pressure event in accordance with an aspect of the present invention. The phrase "transient pressure event," is intended to encompass any occurrence within or outside of a living body that temporarily alters the pressure of a region of interest within the body from a baseline pressure. In general, the alteration in pressure during a transient pressure event will be a temporary increase in pressure, but it will be understood that, in some applications, a temporary decrease in pressure can represent a transient pressure event. It will be appreciated that different regions of interest will have different transient pressure events, and thus the range of possible transient pressure events will vary with the application intended for the system. In an exemplary implementation for a urological application, the region of interest can include the interior of a patient's bladder, urethra, or rectum, and possible transient pressure events can include coughing, sneezing, or engaging in Valsalva maneuver by the patient. In general, the pressure determined by the system 10 will represent a peak pressure associated with a given transient pressure event, where a peak pressure is a maximum or minimum pressure associated with the event.

The system 10 includes an air-charged pressure sensing catheter 20 that can be at least partially inserted into a body of the patient, for example, through an incision or a natural orifice, to monitor the pressure within the region of interest. In the air-charged pressure sensing catheter 20, a contact surface 22 of the air-charged catheter can be inserted into the region of interest, such that a medium (e.g., fluid, soft tissue, air, etc.) within the region of interest can exert pressure on the contact surface. The interior of the contact surface can be charged with a small volume of air to allow for transmission of the pressure exerted by the medium to a transducer 24 located outside of the region of interest. The transducer 24 measures the transmitted pressure during the transient pressure event and provides a series of pressure measurements representing the transient pressure event to a diagnostic measurement system 30.

The measurement system 30 receives the pressure measurements from the air-charged catheter and transforms the pressure data into a form useful to a human operator. It will be appreciated that the measurement system 30 can be implemented as software stored on a non-transitory computer readable medium and operating on a general purpose processor, dedicated hardware, programmable logic devices, or some combination of these elements. Further, while the measurement system 30 is illustrated as an integral unit, it will be appreciated that the various functions performed by the system control can be separated into discrete modules that are spatially remote but in communication within one another.

The measurement system 30 comprises a data conditioning element 32 that receives data from the air-charged pressure sensing catheter 20 and places it in an appropriate form for analysis. For example, the data conditioning element 32 can include one or more analog-to-digital converters to convert the pressure measurements into digital form, digital logic to eliminate obviously erroneous samples, and one or more filters to process the data to remove noise and artifact. It will be appreciated, however, that a major advantage of air-charged catheters is the relatively low level of noise and artifact that they provide, such that the filtering and artifact removal functions of the data conditioning element 32 can be somewhat limited.

The conditioned data can be provided to a parameter calculation component 34 that determines one or more parameters representing the transient pressure event from the conditioned data. For example, a peak pressure, $P_{peak}$, associated with the event, that is, a minimum or maximum pressure reached beyond a pre-event baseline, can be determined. Similarly, a time to peak pressure, $T_{PP}$, can be determined as the amount of time necessary to reach the peak pressure. In one implementation, this is measured as the time between the point at which the pressure reaches five percent of the maximum or minimum pressure and the point at which the maximum or minimum pressure is achieved. The calculated parameters and the conditioned pressure data from the data conditioning element 32 can be provided to a user interface 36 to be displayed to an operator.

In accordance with an aspect of the present invention, it has been determined that the pressure response of air-charged catheters differs from that of water-filled and microtip catheters. Specifically, the pressure response of air-charged catheters is overdamped relative to that of other pressure transducers, resulting in a slight delay in the pressure response and a corresponding underestimation of the peak pressure. Since air-charged catheters are a relatively new technology, many of the standard values for diagnosing and monitoring pathological conditions in the medical fields were generated with water-filled or microtip catheters, and are thus difficult to compare to values generated by air-charged pressure sensing catheters. Further, water-filled catheters are still in use, such that values generated by different diagnostic devices can be inconsistent.

To this end, a system in accordance with the present invention can comprise a standardization component 38 that receives the parameters generated by the parameter calculation component 34 and produces a standardized pressure value that is consistent with pressure values generated by water-filled catheters. Specifically, the standardized pressure value, $P_{Std}$, is produced as a function of the peak pressure, $P_{peak}$, determined from the air-charged catheter and the determined time to peak pressure, $T_{PP}$. In one implementation, the standardized pressure value is determined as a product of the peak pressure and a standardization value determined from the time to peak pressure, such that:

$$P_{Std} = \frac{P_{peak} * T_{PP}^{1.184}}{T_{PP}^{1.184} - 0.03} \qquad \text{Eq. 1}$$

where $T_{PP}$ is the time to peak pressure in seconds, $P_{Std}$ is the standardized pressure in cmH$_2$O, and $P_{peak}$ is the peak pressure in cmH$_2$O.

Once the standardized pressure has been calculated, it can be provided to the user interface 36 for display to an operator. The user interface 36 is configured to receive pressure data from each of the data conditioning element 32, the parameter calculation component 34, and the standardization component 38 and provide the pressure data to an associated display 42 in a form accessible to a human operator. For example, the pressure data can be displayed as one or more charts and tables at the display. The user interface 36 further interprets input from a user at one or more input devices 44 to allow the operator to control the operation of the measurement system 30 and the display of data at the display 42.

Figure 2:
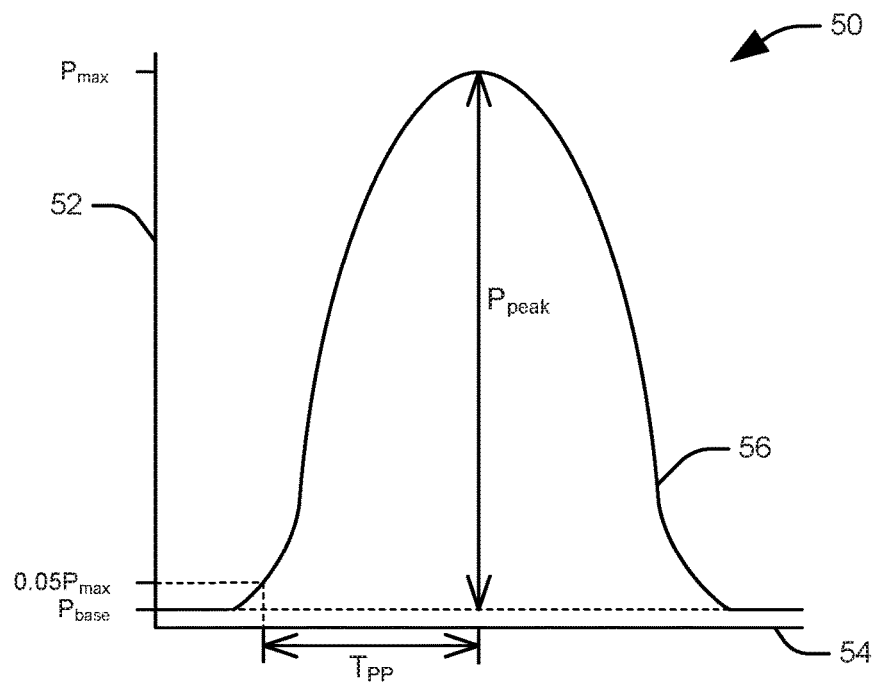
FIG. 2 provides a graphical illustration of the calculation of pressure parameters from the recorded pressure for a given event.

FIG. 2 provides a graphical illustration of the calculation of pressure parameters from the recorded pressure for a given event. The chart 50 includes a vertical axis 52, representing pressure within the region of interest, and a horizontal axis 54, representing time. A trace 56 represents the change in pressure recorded by the air-charged catheter over time immediately before and during a transient pressure event. It will be appreciated that the trace 56 illustrated in FIG. 2 is simplified for the purpose of illustration, and that actual pressure data from a recorded event can be significantly more complex than the smooth, symmetrical trace illustrated in FIG. 2. As can be seen from the chart 50, the trace begins at a baseline pressure, $P_{base}$, prior to a transient pressure event. During the event, the pressure recorded by the air-charged climbs to a maximum value, $P_{max}$, and returns to the baseline pressure.

A peak pressure associated with the event, $P_{peak}$, can be determined as the pressure achieved above the baseline during the event, such that:

$$P_{peak} = P_{max} - P_{base} \qquad \text{Eq. 2}$$

In accordance with an aspect of the present invention, it has been determined that due to the overdamped nature of the air-charged catheter, the time necessary to achieve the peak pressure contributes to a clinical interpretation of the pressure recorded during a transient pressure event. To this end, a time to peak pressure, $T_{PP}$, can be determined as the length of time necessary for the pressure to increase from five percent of the maximum recorded pressure, $0.05 P_{max}$, to the maximum pressure, $P_{max}$. Once this value has been determined, a standardized pressure representing the event can be determined as described previously.

Figure 3:
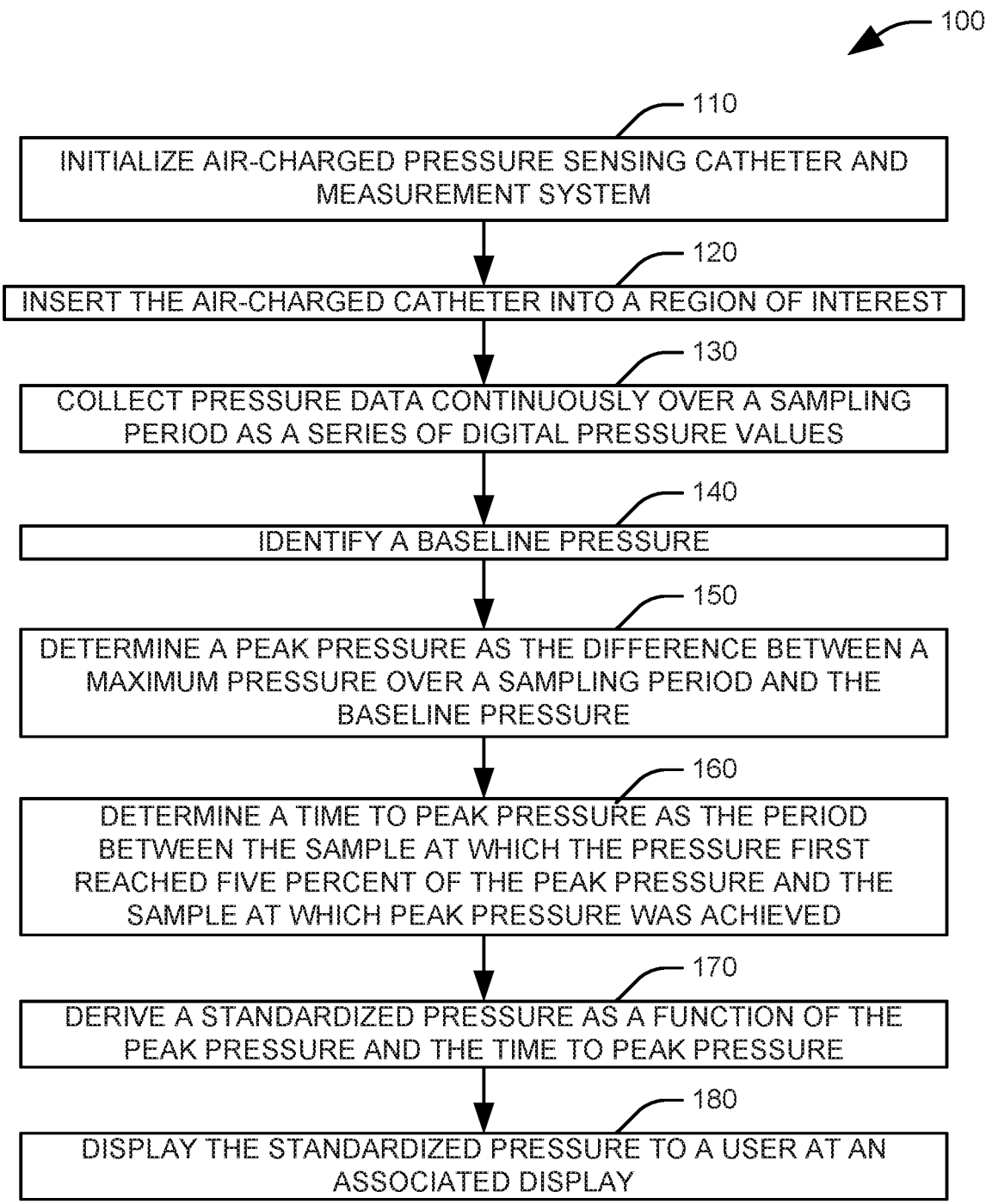
FIG. 3 illustrates a methodology for recording a standardized pressure representing a transient pressure event inside a region of interest with an air-charged catheter in accordance with an aspect of the present invention.

In view of the foregoing structural and functional features described above, methodologies in accordance with various aspects of the present invention will be better appreciated with reference to FIG. 3. While, for purposes of simplicity of explanation, the methodology of FIG. 3 is shown and described as executing serially, it is to be understood and appreciated that the present invention is not limited by the illustrated order, as some aspects could, in accordance with the present invention, occur in different orders and/or concurrently with other aspects from that shown and described herein. Moreover, not all illustrated features may be required to implement a methodology in accordance with an aspect of the present invention.

FIG. 3 illustrates a methodology 100 for recording a standardized pressure representing a transient pressure event inside a region of interest with an air-charged pressure sensing catheter in accordance with an aspect of the present invention. The methodology 100 begins at step 110, where the air-charged catheter and an associated measurement system are initialized. For example, the air-charged catheter can be calibrated and a computer-implemented measurement system for the catheter can be setup and prepared to record measurements from the catheter. At step 120, the air-charged catheter is inserted into a region of interest within a living body. For example, the catheter can be inserted into a urethra or a bladder of a human patient.

At step 130, pressure data from the region of interest is collected as a series of digital pressure values over a period of time including a transient pressure event. For example, the transient pressure event can include a cough, sneeze, or Valsalva maneuver by the patient that changes the pressure within the region of interest for a brief time. At step 140, a baseline pressure, representing the pressure prior to the transient pressure event, can be determined from the recorded pressure data. For example, the baseline pressure can be identified as the pressure prior to a known time of the transient pressure event or the pressure at a region of relatively constant pressure representing an extended period of time.

At step 150, a peak pressure representing the transient pressure event can be determined from the recorded pressure data. For example, a maximum pressure recorded during the event can be determined, and a peak pressure can be calculated as the difference between the maximum pressure and the determined baseline pressure. At step 160, a time to peak pressure is determined to characterize the time response of the air-charged catheter to the transient pressure event. To this end, the start of the event is represented as the point at which the pressure reaches five percent of the maximum pressure, and the time to peak pressure is measured as the time between this point and the point at which a maximum pressure is achieved.

At step 170, a standardized pressure, representing the pressure value that would be expected from a water-filled catheter given the value provided by the air-charged catheter, is calculated as a function of the determined peak pressure and the determined time to peak pressure. For example, the standardized pressure can be calculated as the product of the peak pressure and a function of the time to peak pressure. Once the standardized pressure has been determined, it is displayed in a form comprehensible to a human operator at an associated display at step 180.

Figure 4:
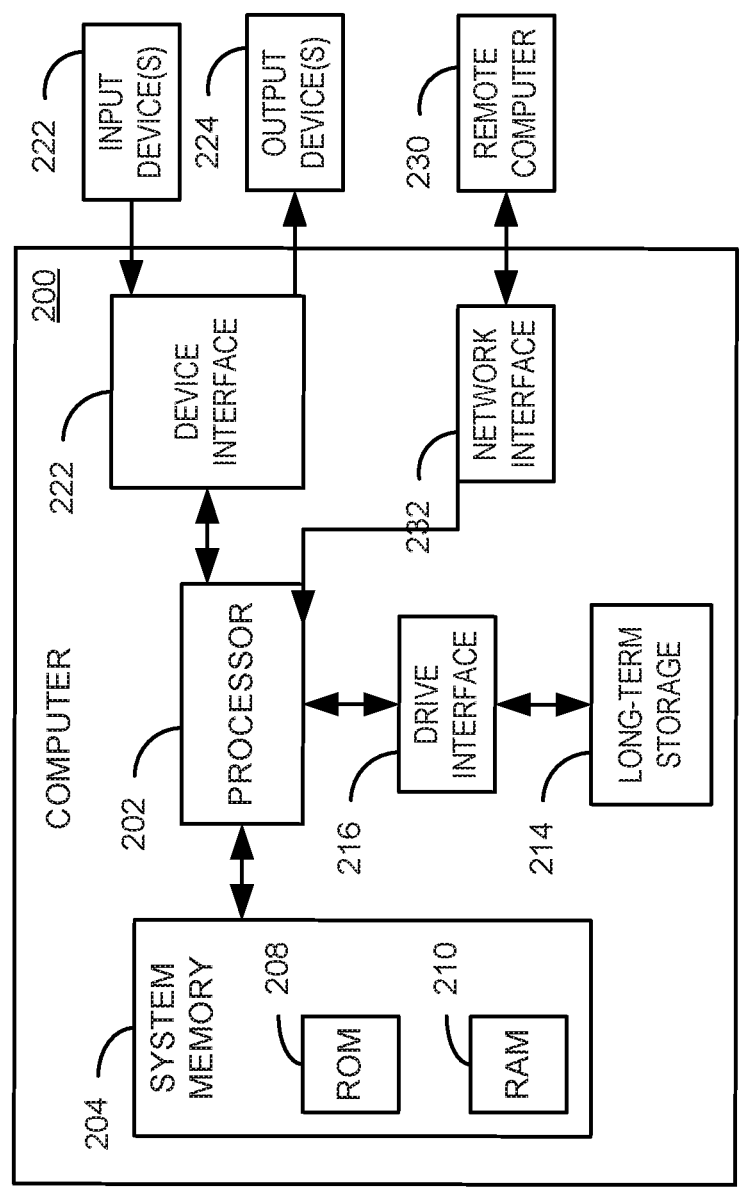
FIG. 4 illustrates a computer system that can be employed to implement systems and methods described herein.

FIG. 4 illustrates a computer system 200 that can be employed to implement systems and methods described herein, such as based on computer executable instructions running on the computer system. The computer system 200 can be implemented on one or more general purpose networked computer systems, embedded computer systems, routers, switches, server devices, client devices, various intermediate devices/nodes and/or stand alone computer systems. Additionally, the computer system 200 can be implemented as part of the computer-aided engineering (CAE) tool running computer executable instructions to perform a method as described herein.

The computer system 200 includes a processor 202 and a system memory 204. Dual microprocessors and other multiprocessor architectures can also be utilized as the processor 202. The processor 202 and system memory 204 can be coupled by any of several types of bus structures, including a memory bus or memory controller, a peripheral bus, and a local bus using any of a variety of bus architectures. The system memory 204 includes read only memory (ROM) 208 and random access memory (RAM) 210. A basic input/output system (BIOS) can reside in the ROM 208, generally containing the basic routines that help to transfer information between elements within the computer system 200, such as a reset or power-up.

The computer system 200 can include one or more types of long-term data storage 214, including a hard disk drive, a magnetic disk drive, (e.g., to read from or write to a removable disk), and an optical disk drive, (e.g., for reading a CD-ROM or DVD disk or to read from or write to other optical media). The long-term data storage can be connected to the processor 202 by a drive interface 216. The long-term storage components 214 provide nonvolatile storage of data, data structures, and computer-executable instructions for the computer system 200. A number of program modules may also be stored in one or more of the drives as well as in the RAM 210, including an operating system, one or more application programs, other program modules, and program data.

A user may enter commands and information into the computer system 200 through one or more input devices 220, such as a keyboard or a pointing device (e.g., a mouse). These and other input devices are often connected to the processor 202 through a device interface 222. For example, the input devices can be connected to the system bus by one or several parallel ports, a serial port or a universal serial bus (USB). One or more output device(s) 224, such as a visual display device or printer, can also be connected to the processor 202 via the device interface 222.

The computer system 200 may operate in a networked environment using logical connections (e.g., a local area network (LAN) or wide area network (WAN) to one or more remote computers 230. A given remote computer 230 may be a workstation, a computer system, a router, a peer device or other common network node, and typically includes many or all of the elements described relative to the computer system 200. The computer system 200 can communicate with the remote computers 230 via a network interface 232, such as a wired or wireless network interface card or modem. In a networked environment, application programs and program data depicted relative to the computer system 200, or portions thereof, may be stored in memory associated with the remote computers 230.

From the above description of the invention, those skilled in the art will perceive improvements, changes and modifications. Such improvements, changes and modifications within the skill of the art are intended to be covered by the appended claims.

Having described the invention, we claim:

1. A method for recording a standardized pressure representing a transient pressure event inside a region of interest with an air-charged pressure sensing catheter comprising:
   inserting the air-charged catheter into the region of interest;
   collecting pressure data with the air-charged catheter over a time period including the transient pressure event to provide a set of pressure data;
   determining a peak pressure in the set of pressure data as the difference between a maximum pressure and a baseline pressure;
   calculating the standardized pressure, representing a peak pressure that would be expected for a water-filled catheter given the determined peak pressure from the set of pressure data collected with the air-charged catheter, as a function of the determined peak pressure; and
   displaying at least the standardized pressure to an operator at an associated display.

2. The method of claim 1, further comprising determining a time to peak pressure as a length of time necessary for the pressure to increase from five percent of the maximum pressure to the maximum pressure.

3. The method of claim 2, wherein calculating the standardized pressure as a function of the determined peak pressure comprises calculating the standardized pressure as a function of the determined peak pressure and the time to peak pressure.

4. The method of claim 3, wherein calculating the standardized pressure as a function of the determined peak pressure and the time to peak pressure comprises calculating the standardized pressure as the product of the determined peak pressure and a ratio of an exponential function of the time to peak pressure to the difference between the exponential function of the time to peak pressure and a predetermined constant.

5. The method of claim 1, further comprising:
   calibrating the air-charged catheter; and
   initializing a computer-implemented measurement system as to prepare the measuring system to record measurements from the catheter.

6. The method of claim 1, further comprising instructing a patient to perform one of a cough, a sneeze, and a Valsalva maneuver during the time period over which the data is collected.

7. The method of claim 1, wherein the region of interest is one of a urethra and a bladder of a patient.

8. A non-transitory computer readable medium storing machine executable instructions for providing a standardized pressure value from pressure data representing a transient pressure event within a region of interest within a living body collected with an air-charger catheter, the machine executable instructions being executable by an associated processor to perform a method comprising:
   determining at least a peak pressure, $P_{peak}$, representing a maximum recorded pressure, in centimeters of water, in the pressure data collected with the air-charged catheter during the transient pressure event and a time to peak pressure, $T_{PP}$, representing a time necessary to reach the peak pressure at the air-charged catheter, from the pressure data collected with the air-charged catheter; and
   calculating the standardized pressure value, $P_{Std}$, representing a peak pressure that would be expected for a water-filled catheter given the peak pressure determined from the pressure data collected with the air-charged catheter, such that:

$$P_{Std} = \frac{P_{peak} * T_{PP}^{1.184}}{T_{PP}^{1.184} - 0.03}.$$

9. The non-transitory computer readable medium of claim 8, wherein determining the peak pressure comprises determining the peak pressure as a difference between a baseline pressure and the maximum recorded pressure at the air-charged catheter and determining the time to peak pressure comprises determining the time to peak pressure as a length of time necessary for the pressure to increase from five percent of the maximum recorded pressure to the maximum recorded pressure.

10. The non-transitory computer readable medium of claim 8, the method further comprising communicating at least the standardized pressure value to an associated display.

* * * * *